(12) United States Patent
Youn et al.

(10) Patent No.: US 12,059,143 B2
(45) Date of Patent: Aug. 13, 2024

(54) SURGICAL PROTECTIVE EQUIPMENT

(71) Applicant: SEOUL NATIONAL UNIVERSITY R&DB FOUNDATION, Seoul (KR)

(72) Inventors: Yeo Kyu Youn, Seoul (KR); Kyu Eun Lee, Seoul (KR); Hyeong Won Yu, Seoul (KR); June Young Choi, Seongnam-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 1134 days.

(21) Appl. No.: 16/961,931

(22) PCT Filed: Oct. 5, 2018

(86) PCT No.: PCT/KR2018/011761
§ 371 (c)(1),
(2) Date: Jul. 14, 2020

(87) PCT Pub. No.: WO2019/078519
PCT Pub. Date: Apr. 25, 2019

(65) Prior Publication Data
US 2022/0000465 A1    Jan. 6, 2022

(30) Foreign Application Priority Data

Oct. 16, 2017   (KR) ........................ 10-2017-0134090

(51) Int. Cl.
*A61B 17/02*    (2006.01)
*A61B 90/00*    (2016.01)

(52) U.S. Cl.
CPC .............. *A61B 17/02* (2013.01); *A61B 90/04* (2016.02); *A61B 2090/0427* (2016.02)

(58) Field of Classification Search
CPC . A61B 17/02; A61B 17/0218; A61B 17/0231; A61B 17/0293; A61B 2017/0212
See application file for complete search history.

(56) References Cited

U.S. PATENT DOCUMENTS 5,267,553 A * 12/1993 Graether ................. A61F 9/007
                                                         623/4.1
5,374,272 A * 12/1994 Arpa .................. A61B 17/0231
                                                         606/107

(Continued)

FOREIGN PATENT DOCUMENTS

JP         3062106 U       9/1999
JP      2012-055716 A      3/2012

(Continued)

OTHER PUBLICATIONS

International Search Report for PCT/KR2018/011761 mailed Jan. 2, 2019 from Korean Intellectual Property Office.

*Primary Examiner* — Nicholas W Woodall
(74) *Attorney, Agent, or Firm* — Revolution IP, PLLC (57) ABSTRACT

A surgical protective equipment includes: a first boundary surface having a horseshoe shape in a plan view; a second boundary surface disposed face-to-face with the first boundary surface and having a horseshoe shape in a plan view; an inner surface disposed between the first boundary surface and the second boundary surface, and forming a groove by connecting an inner end of the first boundary surface and an inner end of the second boundary surface to each other; and an outer surface connecting an outer end of the first boundary surface and an outer end of the second boundary surface, wherein a surgical incision area is inserted in the groove.

6 Claims, 12 Drawing Sheets

(56) References Cited

U.S. PATENT DOCUMENTS

| | | | | |
|---|---|---|---|---|
| 5,433,190 | A * | 7/1995 | Sunalp | A61B 17/0231 606/107 |
| 6,068,643 | A * | 5/2000 | Milverton | A61B 17/0231 606/107 |
| 6,648,819 | B2 * | 11/2003 | Lee | A61B 17/0231 606/107 |
| 8,936,550 | B2 * | 1/2015 | Urano | A61B 17/0231 600/206 |
| 2004/0225265 | A1 | 11/2004 | Tapadiya | |
| 2015/0351736 | A1 * | 12/2015 | Bhattacharjee | A61B 17/0231 600/209 |
| 2016/0199052 | A1 | 7/2016 | Ahluwalia et al. | |
| 2018/0296206 | A1 | 10/2018 | Chung | |

FOREIGN PATENT DOCUMENTS

| | | |
|---|---|---|
| KR | 20-0443479 Y1 | 2/2009 |
| KR | 10-1592975 B1 | 2/2016 |
| KR | 10-2016-0054913 A | 5/2016 |

* cited by examiner

SURGICAL PROTECTIVE EQUIPMENT

TECHNICAL FIELD

The present invention relates to surgical protective equipment, and more particularly, to surgical protective equipment capable of preventing a surgical incision site from being damaged.

BACKGROUND ART

In general, in a surgical operation in which skin needs to be incised, a surgical incision site is exposed such that the surgical incision site may be infected with bacteria. Also, in the case of infection by a cut, complications such as hematomas and the like, cancer surgery, or the like, cancer cells are separated from tumors during a surgical operation and attached to a surgical incision site such that a cancer may metastasize.

In consideration of such a problem, surgical pads (thick sterilized gauze having absorbency to absorb blood shed in a surgical operation, which are temporarily inserted into a surgical site to prevent organs, in addition to the surgical site, from being damaged and absorb and wipe blood at the surgical site) have been used to provide an operating surgeon with a good surgical operation view with respect to the surgical site during the surgical operation but they have the following disadvantages.

When a thick surgical pad is applied to a surgical site, it is necessary to make an unnecessarily large incision to provide a space into which the surgical pad is inserted. Accordingly, a scar is great and recovery of a wound site is delayed such that suffering of a patient increases.

Also, since surgical pads are applied for hemostasis of a surgical site as a main aim such that a surgical incision site is generally exposed during a surgical operation, the surgical incision site is infected through contaminated air and the like or surgical extractions of infected internal organs come into contact with the surgical incision site during a surgical operation on internal organs such that there is a problem of complications.

Also, in the case of cancer surgery, there is a risk that cancer cells are attached to an incision surface. Since there is no additional structure for protecting the incision surface when a field of view is secured by pulling a surgical incision site using a retractor and the like, a possibility of the incision surface being damaged by the retractor itself is present.

Also, although retractors and the like including a material such as polyethylene, vinyl, and the like have partially been used for the above purpose, when surgical instruments using an ultrasonic cutter and the like are used, polyethylene, vinyl, and the like are melted by heat generated at the surgical instruments so that additional damage occurs in the surgical incision site.

Accordingly, surgical protective equipment capable of allowing an operating surgeon to precisely fix the surgical incision site to protect a surgical incision site from external influences as well as preventing the surgical incision site from being burnt by heat is necessary.

DISCLOSURE

Technical Problem

The present invention is directed to providing surgical protective equipment capable of protecting a surgical incision site from bacterial infection, a damage caused by an external force, an injury caused by burns, and the like during a surgical operation.

The present invention is also directed to providing surgical protective equipment capable of stably securing a surgical operation view by minimizing a change or deviation of the surgical protective equipment, which surrounds the surgical incision site, in position thereof when a physical force is applied to the surgical protective equipment during a surgical operation.

However, technical aspects of the embodiment are not limited to the above-described technical aspects and other technical aspects may also be present.

Technical Solution

One aspect of the present invention provides surgical protective equipment including a first rim surface having a horseshoe shape in a plan view, a second rim surface disposed to face the first rim surface and having a horseshoe shape in a plan view, an inner surface disposed between the first rim surface and the second rim surface and configured to form a groove by connecting an inner end of the first rim surface and an inner end of the second rim surface to each other, and an outer surface configured to connect an outer end of the first rim surface and an outer end of the second rim surface to each other. Here, a surgical incision site is inserted into the groove.

The surgical protective equipment may be manufactured in a variety of sizes which vary according to a size of a surgical incision site.

The outer surface may include a first outer surface adjacent to the first rim surface and a second outer surface adjacent to the second rim surface.

Widths of a right side and a left side of the first outer surface may be greater than an upper width of the first outer surface. Also, widths of a right side and a left side of the second outer surface may be greater than an upper width of the second outer surface.

The first outer surface and the second outer surface may have curved shapes.

The first rim surface and the second rim surface may have convex shapes in a downward direction in a left side view and a right side view. The first rim surface and the second rim surface may have convex shapes in an upward direction in a front view and a rear view.

The first rim surface and the second rim surface may have linear shapes in a left side view, a right side view, a front view, and a rear view.

Advantageous Effects

The present invention may allow a surgical incision site to be inserted while being quickly and precisely surrounded to be fixed during a surgical environment to be quickly performed so as to protect a surgical incision site from bacterial infection and wounds caused by skin burns.

Also, since it is possible to protect the surgical incision site by merely inserting the surgical incision site into a groove, a surgical operation may be stably performed with simple manipulation. Particularly, since it is possible to quickly fix the surgical incision site as well as easily secure a surgical operation view, the surgical incision site may be effectively protected and a surgical operation time may be considerably reduced.

According to the aspects of the present application, when a light transmitting material is used, since an operating surgeon may observe bleeding at an incision surface, it is possible to precisely recognize a hemostasis state of the incision surface.

MODES OF THE INVENTION

Hereinafter, embodiments of the present application will be described with reference to the attached drawings to be easily performed by one of ordinary skill in the art. However, the present application may be implemented in a variety of shapes and will not be limited to the embodiments described herein. Also, throughout the drawings, for clear description of the present application, irrelevant parts will be omitted. Throughout the specification, like elements will be referred to as like reference numerals.

Throughout the specification, when a part is stated as being "connected" to another part, the part is not only "directly connected" but also "electrically connected" to the other component with another device therebetween.

Throughout the specification, when a member is stated as being located "on" another member, not only the member comes into contact with the other member but also still another member is present therebetween.

Throughout the specification, when a portion is stated as "including" a component, unless particularly defined otherwise, it means that the portion may not exclude another component but may further include another component.

The terms of degree used herein such as "about," "substantially," and the like are used as meanings of numerical values of unique manufacturing and material allowances being provided or being approximate to the numerical values. Also, the terms are used to prevent the disclosed content in which precise or absolute reference numerals are stated to allow the present application to be understood from being abused by unconscientious infringers.

Figure 1:
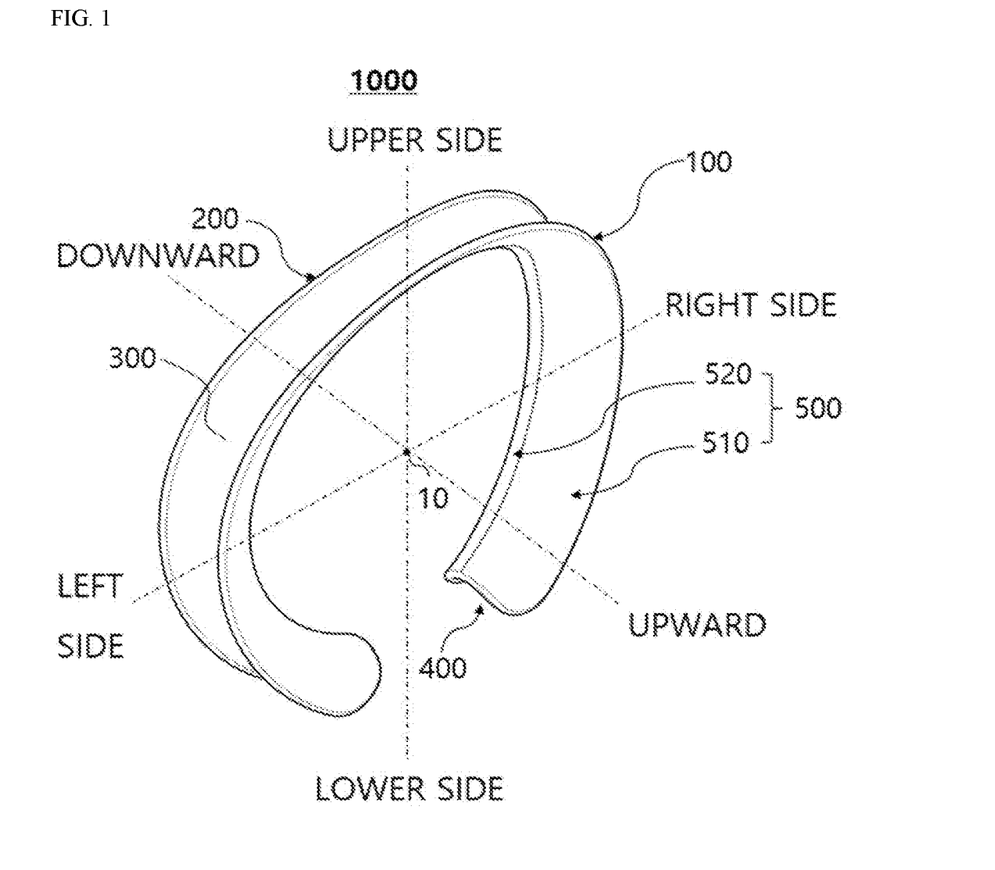
FIG. 1 is a perspective view of surgical protective equipment according to one embodiment of the present invention.
Figure 2:
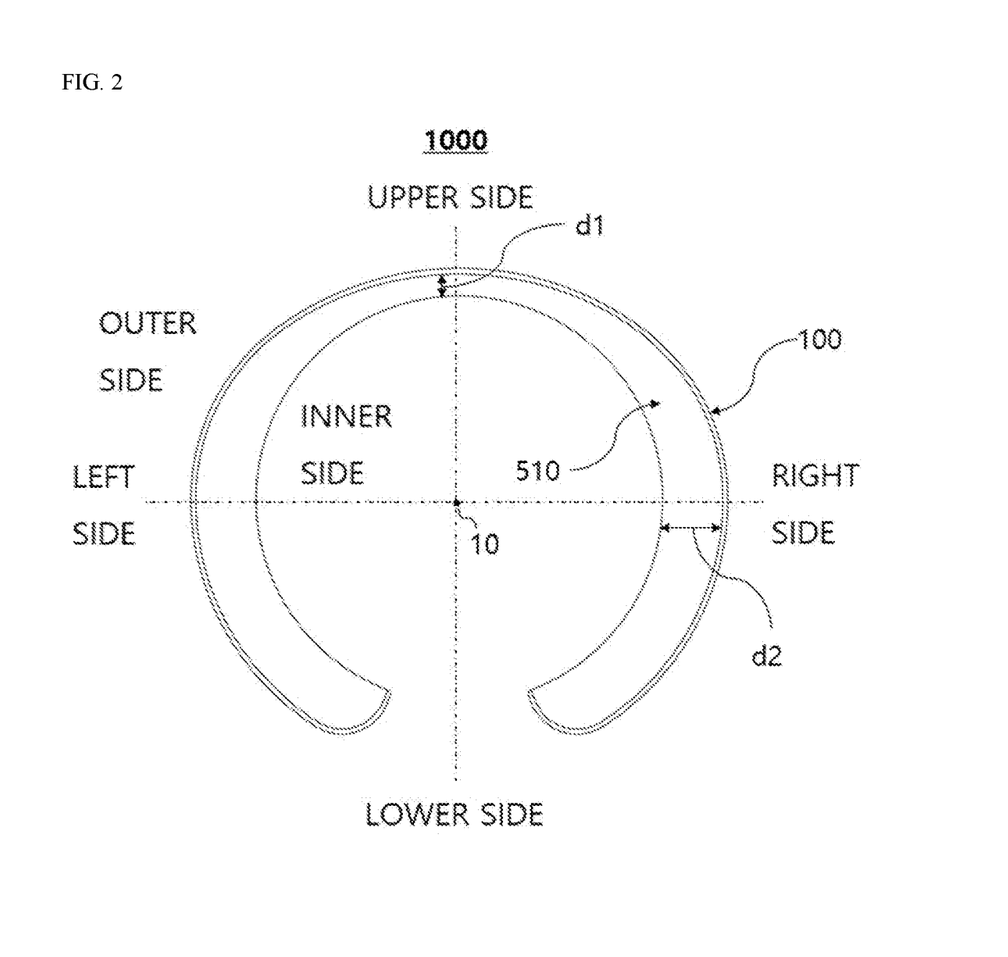
FIG. 2 is a plan view of the surgical protective equipment according to one embodiment of the present invention.
Figure 3:
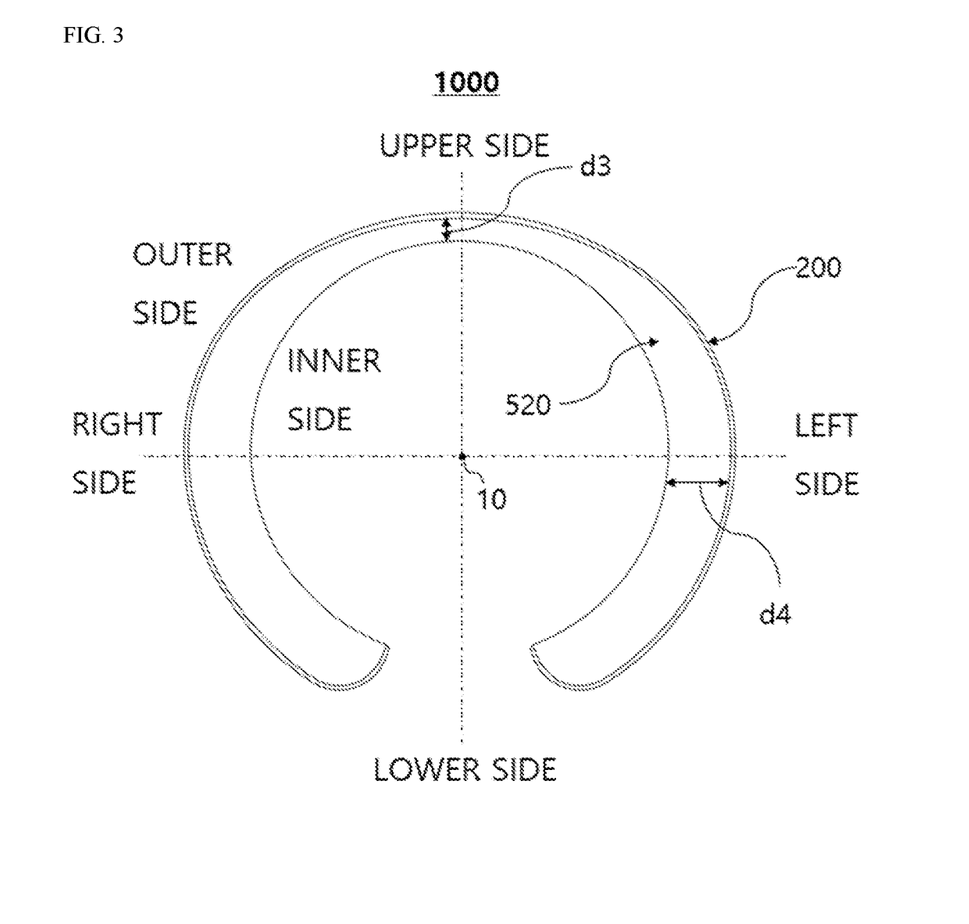
FIG. 3 is a bottom view of the surgical protective equipment according to one embodiment of the present invention.
Figure 4:
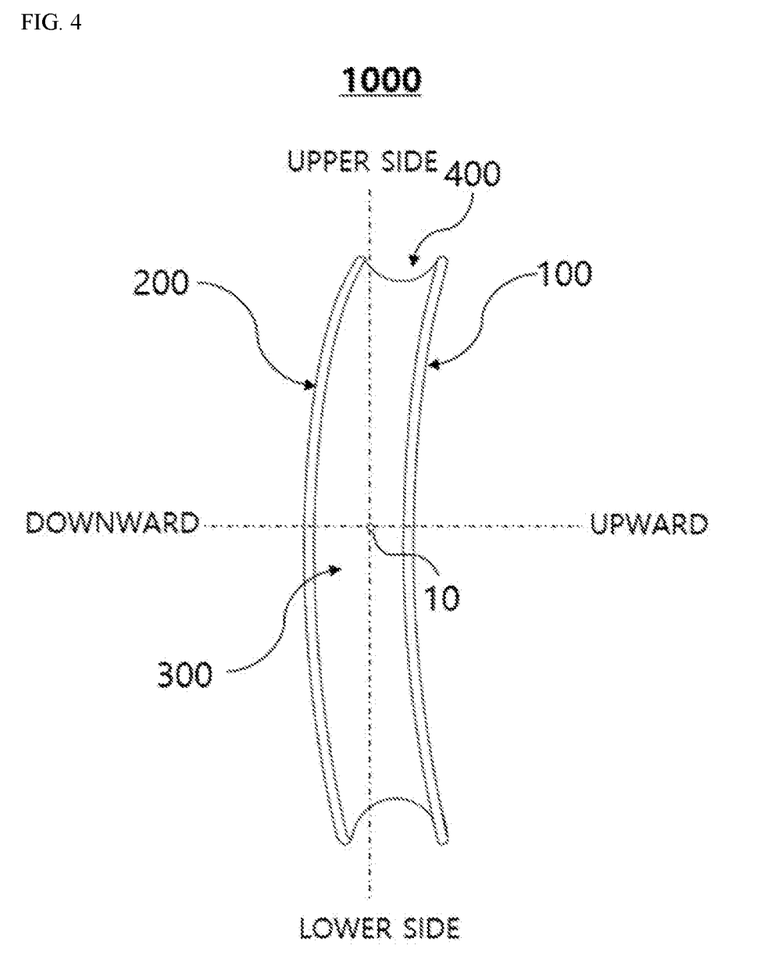
FIG. 4 is a left side view of the surgical protective equipment according to one embodiment of the present invention.
Figure 5:
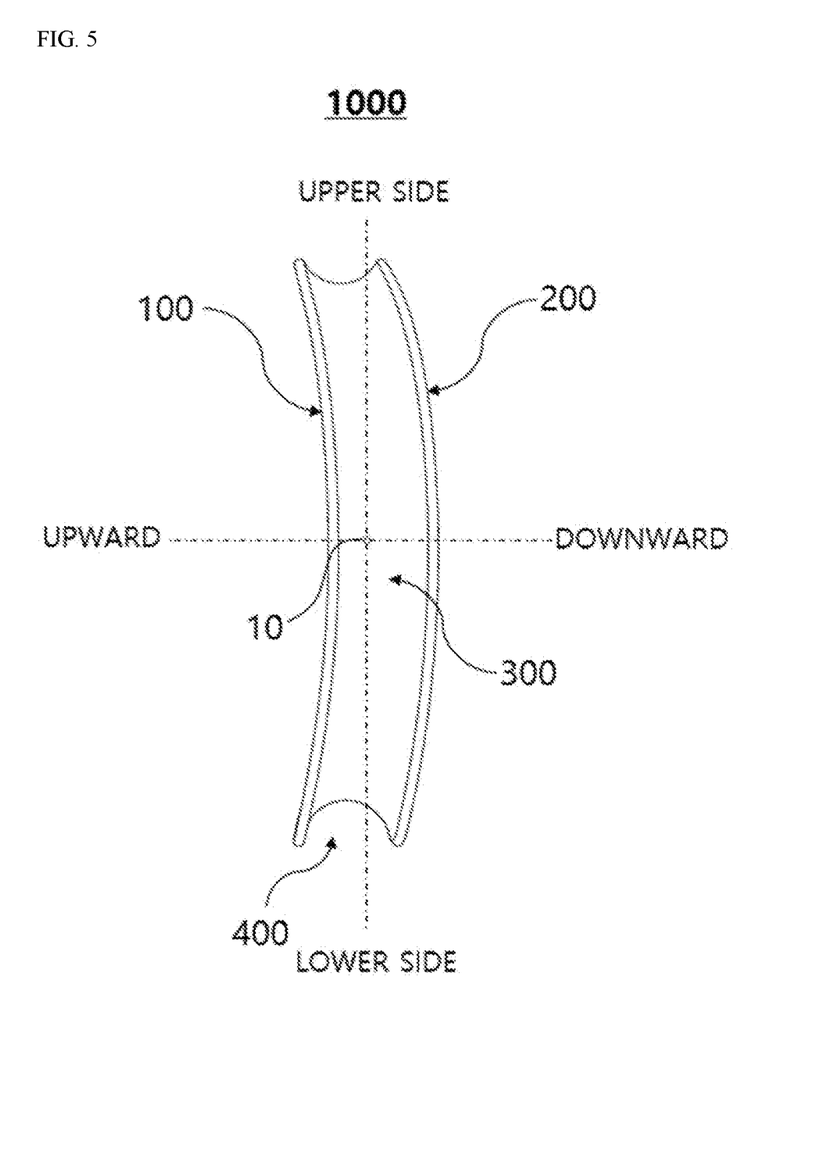
FIG. 5 is a right side view of the surgical protective equipment according to one embodiment of the present invention.
Figure 6:
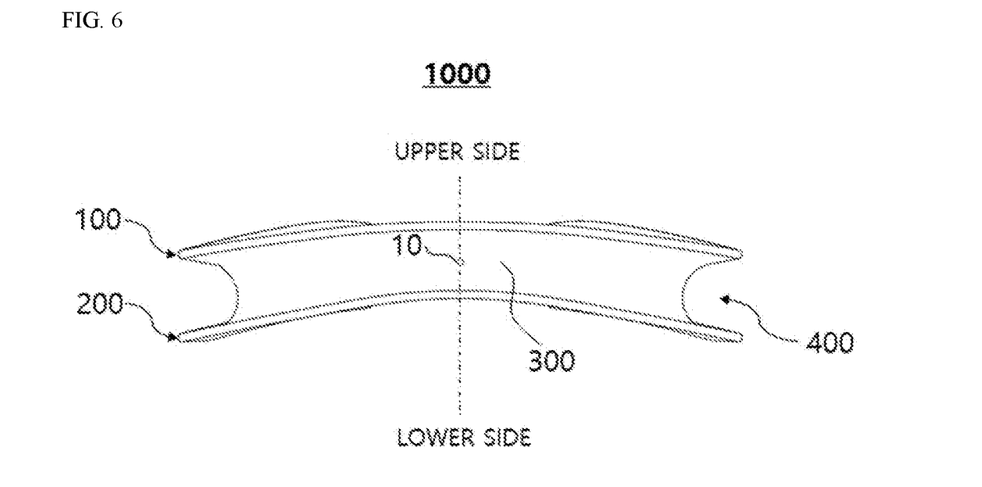
FIG. 6 is a front view of the surgical protective equipment according to one embodiment of the present invention.
Figure 7:
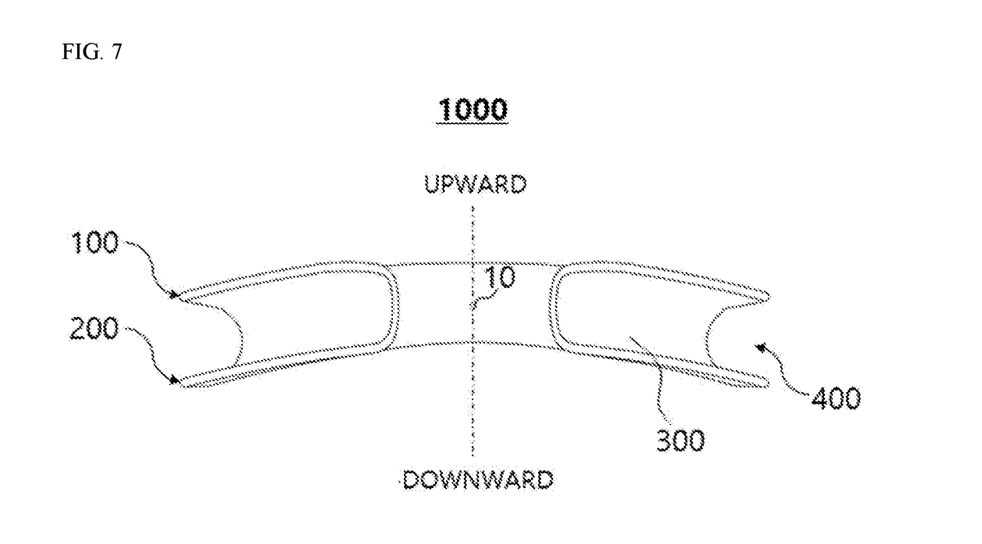
FIG. 7 is a rear view of the surgical protective equipment according to one embodiment of the present invention.

FIG. 1 is a perspective view of surgical protective equipment according to one embodiment of the present invention, FIG. 2 is a plan view of the surgical protective equipment according to one embodiment of the present invention, FIG. 3 is a bottom view of the surgical protective equipment according to one embodiment of the present invention, FIG. 4 is a left side view of the surgical protective equipment according to one embodiment of the present invention, FIG. 5 is a right side view of the surgical protective equipment according to one embodiment of the present invention, FIG. 6 is a front view of the surgical protective equipment according to one embodiment of the present invention, and FIG. 7 is a rear view of the surgical protective equipment according to one embodiment of the present invention.

Referring to FIGS. 1 to 3, surgical protective equipment 1000 according to one embodiment of the present invention may include a first rim surface 100, a second rim surface 200, an inner surface 300, and an outer surface 500.

The first rim surface 100 may have a horseshoe shape in a plan view. The first rim surface 100 refers to a surface viewed in the plan view of the surgical protective equipment according to one embodiment of the present invention and connects the inner surface 300 and the outer surface 500 to each other. The second rim surface 200 may be disposed to face the first rim surface 100 and have a horseshoe shape in a bottom view. The second rim surface 200 refers to a surface viewed in the bottom view of the surgical protective equipment according to one embodiment of the present invention and connects the inner surface 300 and the outer surface 500 to each other.

The surgical protective equipment 1000 according to one embodiment of the present invention may have a partially cut rim shape. That is, a cross section thereof may have a U shape. The first rim surface 100 may extend in a direction from a rim-shaped open area of the surgical protective equipment 1000 toward an internal center point 10. Also, the second rim surface 200 may extend in the direction from the rim-shaped open area of the surgical protective equipment 1000 toward the internal center point 10. Accordingly, the first rim surface 100 and the second rim surface 200 may be formed to meet each other at an open lower side.

The inner surface 300 may be disposed between the first rim surface 100 and the second rim surface 200, and connect an inner end of the first rim surface 100 and an inner end of the second rim surface 200 to each other to form a groove 400. A surgical incision site may be inserted into the groove 400, and the groove 400 may have a U-shaped cross section.

The outer surface 500 may include a first outer surface 510 adjacent to the first rim surface 100 and a second outer surface 520 adjacent to the second rim surface 200. The first outer surface 510 may have a curved shape. A width of the first outer surface 510 may be gradually decreased from a lower side toward an upper side. For example, the upper side of the first outer surface 510 may have a first width d1 and left and right sides thereof may have a second width d2 great than the first width d1. Here, the first width d1 and the second width d2 refer to a distance from a boundary line between the first outer surface 510 and the second outer surface to a boundary line between the first surface 510 and the first rim surface 100.

The second outer surface 520 may have a curved shape. A width of the second outer surface 520 may be gradually decreased from a lower side toward an upper side. For example, the upper side of the second outer surface 520 may have a third width d3 and left and right sides thereof may have a fourth width d4 greater than the third width d3. Here, the third width d3 and the fourth width d4 refer to a distance from a boundary line between the first outer surface 510 and the second outer surface to a boundary line between the second outer surface 520 and the second rim surface 200.

Since the width of the first outer surface 510 and the width of the second outer surface 520 are formed to be gradually decreased from the lower side toward the upper side, a depth of the groove 400 is formed to be decreased from a lower side toward an upper side. Accordingly, the surgical protective equipment 1000 according to one embodiment of the present invention may be formed to have a relatively thin upper side. Also, since the surgical protective equipment 1000 is formed to have the relatively thin upper side, a left side and a right side of the surgical protective equipment 1000 may be easily bent inward on the basis of the lower side.

The surgical protective equipment 1000 according to one embodiment of the present invention is inserted into an incision part of a patient during a surgical operation. Here, since the left side and the right side of the surgical protective equipment 1000 are easily bendable inward on the basis of the lower side, the surgical protective equipment is easily insertable without needing to open a surgical site of the patient. Also, since the surgical protective equipment 1000, which is bent inward, is formed of an elastic material and has a property of returning to an original shape, the surgical protective equipment may be firmly fixed to the surgical site of the patient after insertion.

Since the surgical protective equipment 1000 according to one embodiment of the present invention has a restoration property when a force is applied, the surgical protective equipment 1000 may function to continuously open the surgical site after the surgical protective equipment 1000 is inserted thereinto. Accordingly, it is effective to secure a field of view during the surgical operation and elasticity is provided when a force is applied such that the surgical protective equipment may be easily inserted into the surgical site without an operation of opening the surgical site.

Accordingly, the surgical protective equipment 1000 according to one embodiment of the present invention may be formed of an elastic material to have adequate restorability to continuously open the surgical site of the patient and to be easily inserted into the surgical site. Particularly, so as not to allow the surgical protective equipment to be easily bent due to excessively strong restoring force or so as not to decrease a force of continuously opening the surgical site due to excessively strong elasticity, the surgical protective equipment may be formed of a material in which restorability and elasticity are adequately matched to have an adequate force of continuously opening the surgical site as well as having an adequate elastic force to bend well while being inserted.

Referring to FIGS. 4 to 7, the surgical protective equipment 1000 according to one embodiment of the present invention may have a convex shape in an upward or downward direction depending on a direction of viewing.

The surgical protective equipment 1000 according to one embodiment of the present invention may be formed to have a convex shape in a downward direction in a left side view and a right side view. Accordingly, the first rim surface 100 and the second rim surface 200 may be formed to have a convex shape in a downward direction in a left side view and a right side view.

Also, the surgical protective equipment 1000 according to one embodiment of the present invention may be formed to have a convex shape in an upward direction in a front view and a rear view. Accordingly, the first rim surface 100 and the second rim surface 200 may be formed to have a convex shape in an upward direction in a front view and a rear view.

The surgical protective equipment 1000 according to one embodiment is formed to have a convex shape in a downward direction in the left side view and the right side view and have a convex shape in an upward direction in the front view and the rear view. Accordingly, when the surgical protective equipment 1000 according to one embodiment is used in a thyroidectomy operation, the surgical protective equipment may be firmly fixed to a resected part of a patient due to a shape similar to a human body structure.

Figure 8:
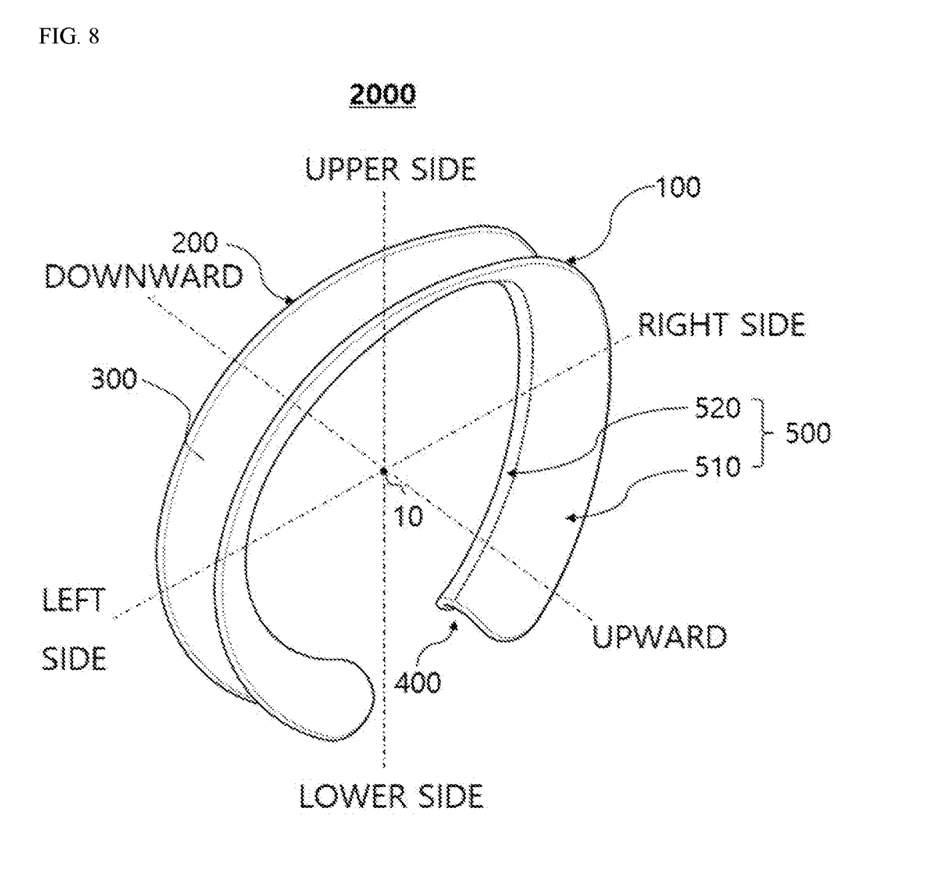
FIG. 8 is a perspective view of surgical protective equipment according to another embodiment of the present invention.
Figure 9:
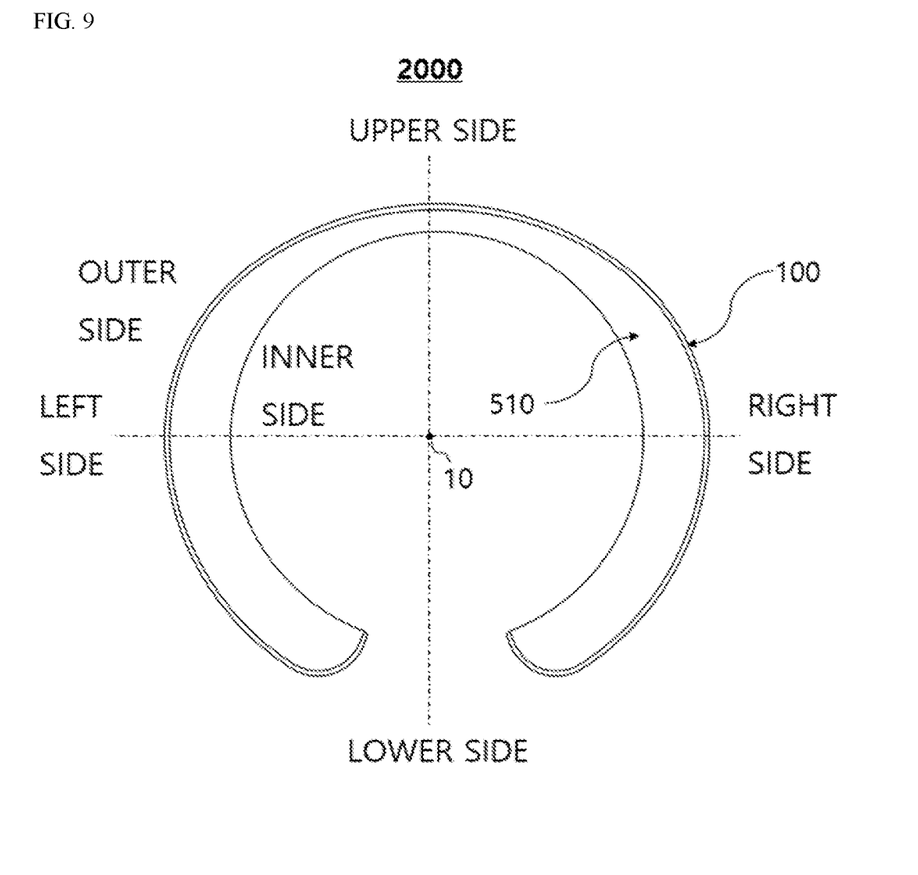
FIG. 9 is a plan view of the surgical protective equipment according to another embodiment of the present invention.
Figure 10:
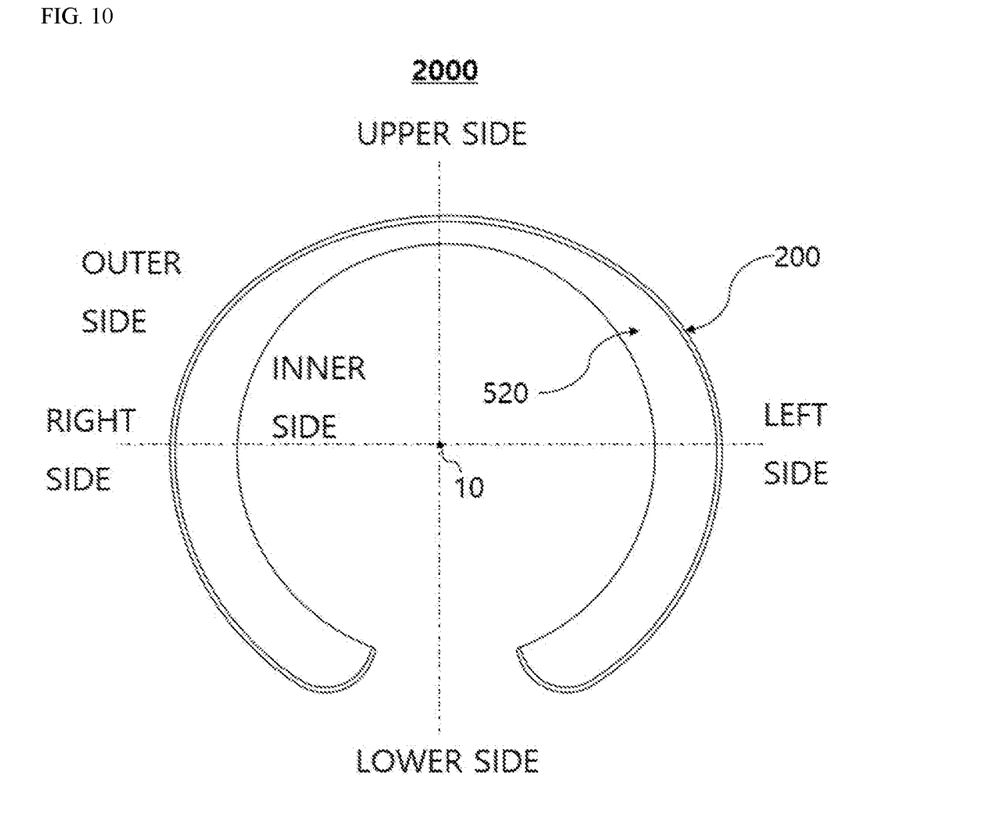
FIG. 10 is a bottom view of the surgical protective equipment according to another embodiment of the present invention.
Figure 11:
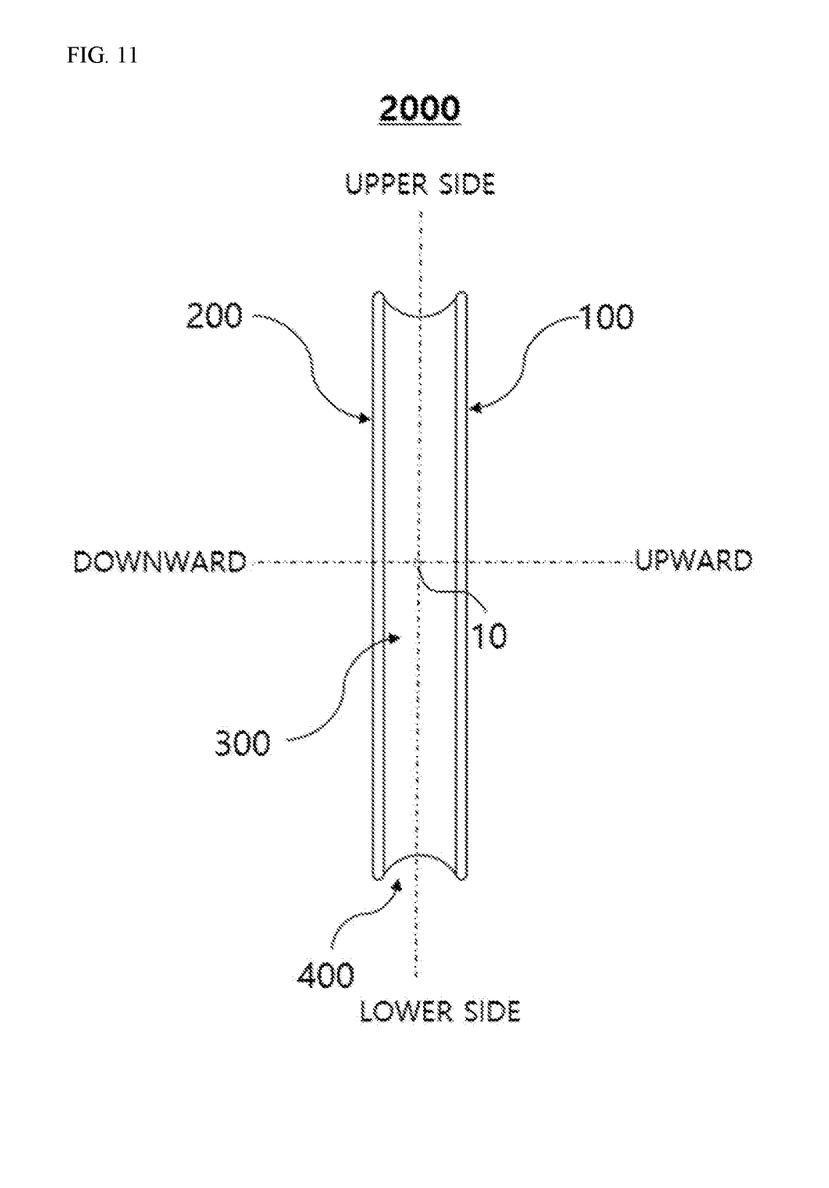
FIG. 11 is a left side view of the surgical protective equipment according to another embodiment of the present invention.
Figure 12:
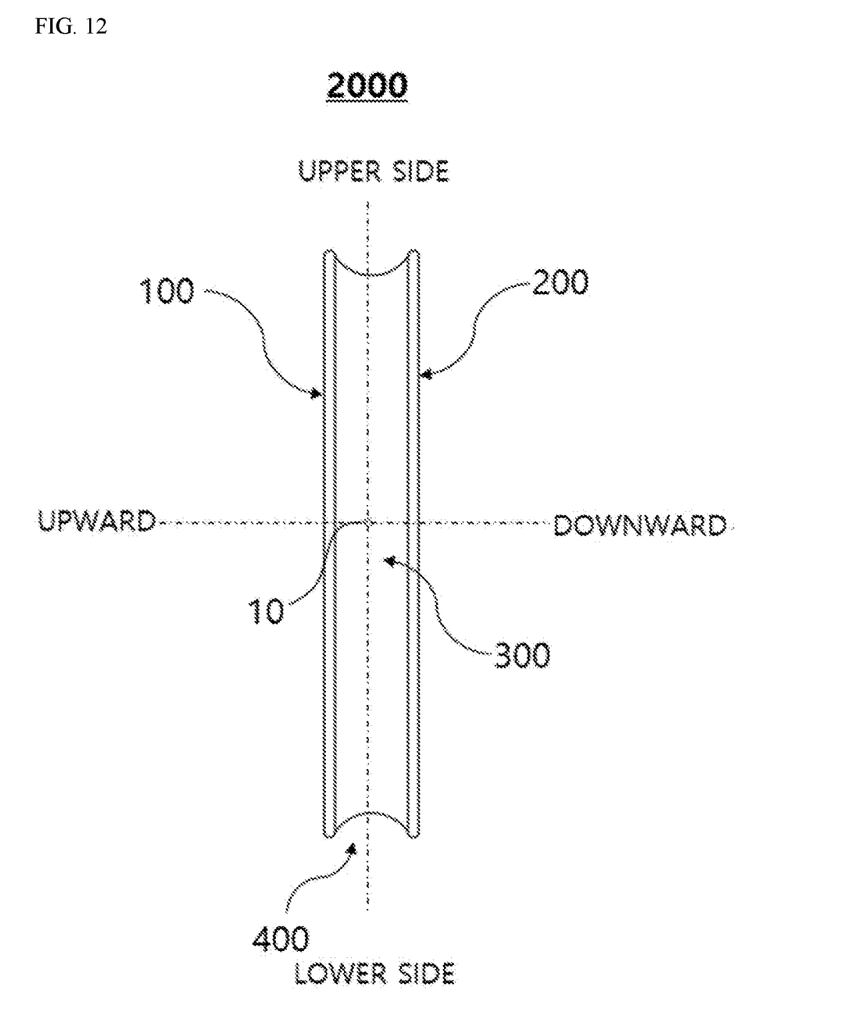
FIG. 12 is a right side view of the surgical protective equipment according to another embodiment of the present invention.
Figure 13:
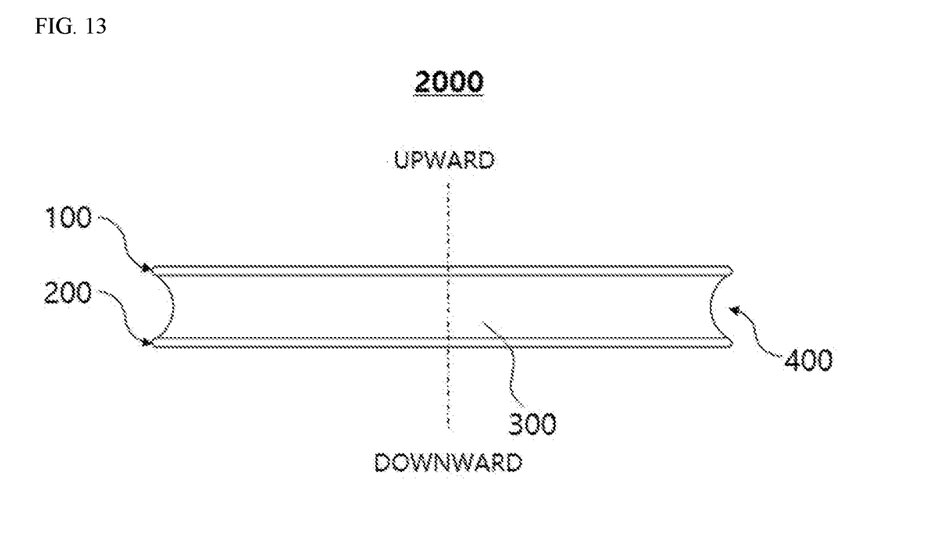
FIG. 13 is a front view of the surgical protective equipment according to another embodiment of the present invention.
Figure 14:
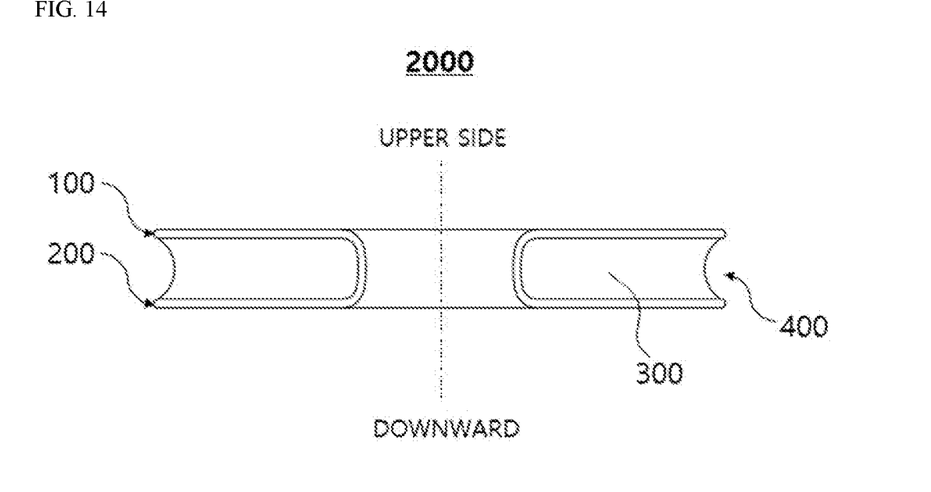
FIG. 14 is a rear view of the surgical protective equipment according to another embodiment of the present invention.

FIG. 8 is a perspective view of surgical protective equipment according to another embodiment of the present invention. FIG. 9 is a plan view of the surgical protective equipment according to another embodiment of the present invention. FIG. 10 is a bottom view of the surgical protective equipment according to another embodiment of the present invention. FIG. 11 is a left side view of the surgical protective equipment according to another embodiment of the present invention. FIG. 12 is a right side view of the surgical protective equipment according to another embodiment of the present invention. FIG. 13 is a front view of the surgical protective equipment according to another embodiment of the present invention. FIG. 14 is a rear view of the surgical protective equipment according to another embodiment of the present invention.

Since surgical protective equipment 2000 according to another embodiment of the present invention is equal to the above-described surgical protective equipment 1000 except that the first rim surface 100 and the second rim surface 200 have linear shapes in the left side view, the right side view, the front view, and the rear view, a detailed description thereof will be omitted.

Referring to FIGS. 8 to 14, the surgical protective equipment 2000 according to another embodiment of the present invention may include the first rim surface 100, the second rim surface 200, the inner surface 300, and the outer surface 500. The first rim surface 100 and the second rim surface 200 of the surgical protective equipment 2000 each have a horseshoe shape and may be disposed to face each other. The inner surface 300 may form the groove 400 by connecting an inner end of the first rim surface 100 and an inner end of the second rim surface 200 to each other.

The surgical protective equipment 2000 according to another embodiment has a linear shape in the left side view, the right side view, the front view, and the rear view. Accordingly, the surgical protective equipment 2000 may be more firmly fixed to an incision surface of a human body part having a relatively flat shape such as abdomen rather than the surgical protective equipment 1000 according to one embodiment of the present invention.

The first rim surface 100, the second rim surface 200, the inner surface 300, and the outer surface 500 of the surgical protective equipment 1000 or 2000 according to the embodiment of the present invention may be integrally formed and include a light transmitting material. The light transmitting material may be understood as a concept including both translucent and completely transparent materials. In the case of the present invention being formed of a light transmitting material, an operating surgeon may observer bleeding at a surgical incision site and a surgical incision surface and may precisely figure out a hemostasis state thereof.

Also, the first rim surface 100, the second rim surface 200, the inner surface 300, and the outer surface 500 of the surgical protective equipment 1000 or 2000 according to the embodiment of the present invention may include an opaque material and additionally include a dye material to be colored. For example, when the surgical protective equipment is colored, a function of limiting use such as limiting use to a particular surgical part or the like may be performed but the present invention is not limited thereto.

Also, the surgical protective equipment 1000 or 2000 according to the embodiment of the present invention may preferably include a material having high thermal resistance so as to prevent the surgical incision site (skin and the like) from being burnt by heat generated by a surgical instrument and to prevent the surgical protective equipment 1000 and 2000 from being deformed by heat or the like.

Also, when the skin is incised and then the incised surgical incision site is inserted into the groove 400, the surgical incision site and the surgical incision surface are inserted into the groove 400 and fixed to the surgical protective equipment 1000 or 2000. When a surgical operation is performed during the above fixed state, it is possible to prevent the surgical incision site or the like from coming into contact with the surgical instrument, which generates heat, or the like such that the surgical incision site and the surgical incision surface are prevented from being burnt. Also, it is possible to prevent the surgical incision site and the surgical incision surface from being exposed outward and being infected and to easily secure a surgical operation view so as to increase convenience of surgical operation.

The above description of the present application is merely an example, and it should be understood that a variety of modifications in other detailed shapes may be easily made by one of ordinary skill in the art without changing a technical concept or essential features of the present application. Therefore, it should be understood that the above-described embodiments are exemplary and not limitative in every aspect. For example, each component which has been described as a single type may be implemented while being dispersed, and similarly, components which have been described as being dispersed may be implemented in an integrated form.

The scope of the present application will be defined by the following claims, and it should be construed that all changes or modifications derived from the meaning and the scope of the claims and equivalents thereof are included in the scope of the present application.

The invention claimed is:

1. Surgical protective equipment for a surgical incision site, comprising:
a first rim surface having a horseshoe shape in a plan view, wherein both ends of the first rim surface are disconnected to each other, the both ends of the first rim surface being defined as first free ends, wherein one end of the first rim surface is gradually extended to the other end of the first rim surface;
a second rim surface disposed to face the first rim surface and having a horseshoe shape in a plan view, wherein both ends of the second rim surface are disconnected to each other, the both ends of the second rim surface being defined as second free ends, wherein one end of the second rim surface is gradually extended to the other end of the second rim surface;
an inner surface disposed between the first rim surface and the second rim surface and configured to form a groove by connecting an inner end of the first rim surface and an inner end of the second rim surface to each other; and
an outer surface configured to connect an outer end of the first rim surface and an outer end of the second rim surface to each other,
wherein the groove is configured to receive the surgical incision site and continuously extends from one end of the right side to the other end of the left side of the groove,
wherein a width of the groove becomes gradually wider from the upper side of the groove toward the right and the left sides of the groove.

2. The surgical protective equipment of claim 1, wherein the outer surface comprises:
a first outer surface adjacent to the first rim surface; and
a second outer surface adjacent to the second rim surface.

3. The surgical protective equipment of claim 2, wherein widths of a right side and a left side of the first outer surface are greater than an upper width of the first outer surface, and
wherein widths of a right side and a left side of the second outer surface are greater than an upper width of the second outer surface.

4. The surgical protective equipment of claim 2, wherein the first outer surface and the second outer surface have curved shapes.

5. The surgical protective equipment of claim 1, wherein the first rim surface and the second rim surface have convex shapes in a downward direction in a left side view and a right side view and have convex shapes in an upward direction in a front view and a rear view.

6. The surgical protective equipment of claim 1, wherein the first rim surface and the second rim surface have linear shapes in a left side view, a right side view, a front view, and a rear view.

* * * * *